(12) United States Patent
Suzuki et al.

(10) Patent No.: US 7,331,945 B2
(45) Date of Patent: Feb. 19, 2008

(54) FOLDED DISPOSABLE DIAPER HAVING INDICIA THAT VISUALLY CHANGE OR BECOME VISIBLE WHEN THE DIAPER IS UNFOLDED

(75) Inventors: Sachiyo Suzuki, Kagawa (JP); Hiroki Ishikawa, Kagawa (JP); Satoru Sakaguchi, Kagawa (JP); Kaori Yuasa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 10/878,684

(22) Filed: Jun. 29, 2004

(65) Prior Publication Data

US 2005/0027274 A1 Feb. 3, 2005

Related U.S. Application Data

(63) Continuation of application No. PCT/JP03/11065, filed on Aug. 29, 2003.

(30) Foreign Application Priority Data

Sep. 18, 2002 (JP) ............................. 2002-272326

(51) Int. Cl.
 *A61F 13/15* (2006.01)
 *A06F 13/20* (2006.01)
(52) U.S. Cl. .................... 604/385.201; 604/385.01; 604/358
(58) Field of Classification Search ........... 604/385.01, 604/358, 385.201, 385.13, 385.19, 385.21, 604/385.22, 385.23
See application file for complete search history.

(56) References Cited

U.S. PATENT DOCUMENTS 5,531,731 A * 7/1996 Brusky ...................... 604/390
5,897,541 A * 4/1999 Uitenbroek et al. ......... 604/358
6,297,424 B1 * 10/2001 Olson et al. ................ 604/361
6,352,528 B1 * 3/2002 Weber et al. ........... 604/385.03
6,733,483 B2 * 5/2004 Raufman et al. ...... 604/385.01

FOREIGN PATENT DOCUMENTS

| | | |
|---|---|---|
| JP | U-62-129005 | 8/1987 |
| JP | A-5-247701 | 9/1993 |
| JP | 6-106839 A | 4/1994 |
| JP | A-2000-27009 | 1/2000 |
| JP | 2000-314020 A | 11/2000 |
| JP | A-2001-54536 | 2/2001 |
| JP | A-2001-73201 | 3/2001 |
| JP | A-2002-95696 | 4/2002 |
| JP | A-2003-501211 | 1/2003 |
| JP | A-2003-509163 | 3/2003 |
| WO | WO 00/35401 A1 | 6/2000 |
| WO | WO 00/76442 A1 | 12/2000 |
| WO | WO 01/21126 | 3/2001 |
| WO | WO 01/49230 | 7/2001 |

* cited by examiner

*Primary Examiner*—Michele Kidwell
(74) *Attorney, Agent, or Firm*—Lowe Hauptman Ham & Berner LLP

(57) ABSTRACT

A disposable diaper is provided such that the disposable diaper has at least one predetermined illustration displayed thereon and is folded into a predetermined shape. The illustration is provided in such a manner that at least a portion of the illustration is hidden when the disposable diaper is folded into the predetermined shape, and the hidden portion of the illustration is exposed as the disposable diaper is unfolded from the folded state.

14 Claims, 12 Drawing Sheets

Fig. 3A    Fig. 3B    Fig. 3C
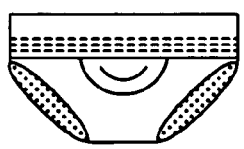  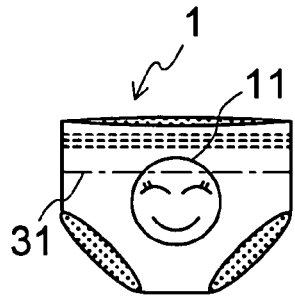 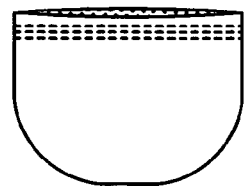
Fig. 4A    Fig. 4B    Fig. 4C
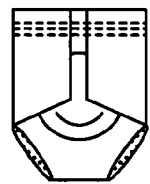  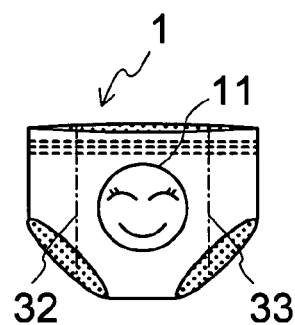 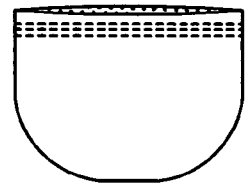
Fig. 5A    Fig. 5B    Fig. 5C
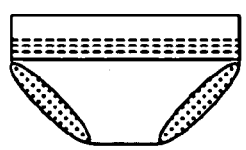  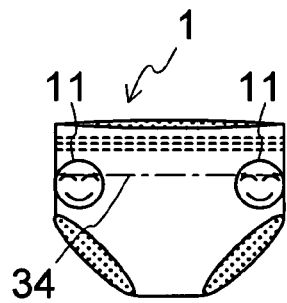 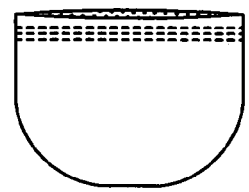

Fig. 28A
Fig. 28B
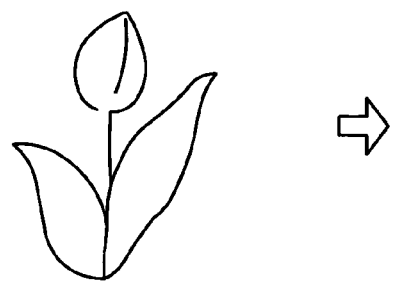
Fig. 29A
Fig. 29B
Fig. 29C
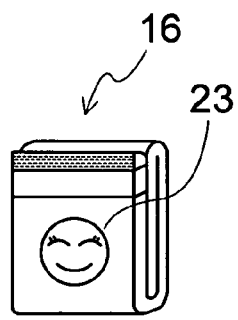 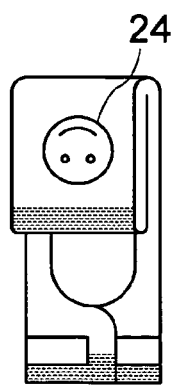 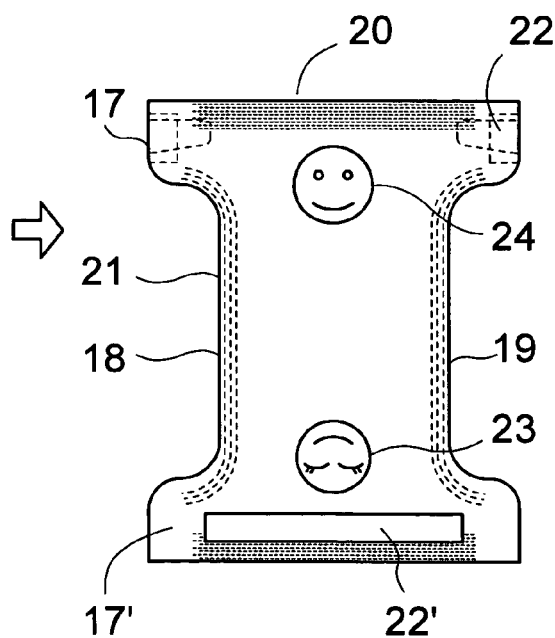

FOLDED DISPOSABLE DIAPER HAVING INDICIA THAT VISUALLY CHANGE OR BECOME VISIBLE WHEN THE DIAPER IS UNFOLDED

CROSS-REFERENCE TO RELATED APPLICATIONS

This application is a Continuation of International Application No. PCT/JP2003/011065 filed Aug. 29, 2003, which application published in Japanese on Apr. 1, 2004 as WO 2004/026206 A1 under PCT Article 21 (2). The International Application PCT/JP2003/011065 is based upon and claims the benefit of priority from Japanese Patent application No.2002-272326 filed on Sep. 18, 2002, the entire contents of which is incorporated herein by reference.

FIELD OF THE INVENTION

The present invention relates to a disposable diaper having at least one illustration displayed thereon and, more specifically, it relates to a disposable diaper having one or more illustrations to be recognized, which vary by unfold the folded disposable diaper.

RELATED ART

It is a significant burden physically and mentally to change disposable diapers for a baby who is fussing about changing disposable diapers. In order to alleviate such a burden, an illustration that is considered to entertain small babies is provided onto the disposable diaper. Disposable diapers with illustrations of pretty characters on the front and back faces are actually circulated.

However, such disposable diapers are not so effective as expected, and a diaper changer still has a burden since babies (in particular, babies or toddlers who can move their arms and legs, crawl, walk, or run) sometimes fuss, cry, or run away to avoid diaper change.

The related art is explained in detail. In International Publication No. WO 01/49230, a diaper having a back sheet made of non-woven fabric that has a light transmittance of 80% or more is disclosed such that it is prevented to reduce an impact of the illustration drawn on the diaper so that a diaper changer entertains a bay and the baby is motivated to undergo potty training.

In International Publication No. WO 01/49230, a training pants for a baby of 15 kg or more in weight is disclosed such that an indicating design which disappears when the pants are wet is employed with the pants in order to give the baby an incentive to practice the potty training.

However, according to the related art as described above, the design of the diaper satisfies only the diaper changer, but does not attract the baby so much as expected. Consequently, the baby is actually distracted by something else.

SUMMARY OF THE INVENTION

In view of the subjects described above, it is an object of the present invention to provide a disposable diaper that is characterized to reduce the burden required for changing diapers by attracting or distracting the baby whose intellectual faculties are grown to a certain extent, not by satisfying the diaper changer.

In order to achieve the above-described object, according to the present invention, at least one illustration is provided on either front or back face, or on both front and back faces of the disposable diaper, and at least a portion of the illustration is hidden in a folded state of the disposable diaper and appears as the folded disposable diaper is unfolded for putting it on the baby. Here, to be unfolded includes to be deployed in the meaning. The disposable diaper is also provided such that the illustration can entertain the baby by changing itself from one recognizable state of the folded disposable diaper to another state while the disposable diaper is unfolded to prepare the diaper change for the baby, and the disposable diaper is provided for babies in a stage of developing intellectual faculties.

As is generally said, an eye sight of the baby is only 0.04-0.08 for babies of six months old, 0.2-0.25 for the babies of twelve months old, and 0.5-0.6 for the babies of twenty-four months old, and thus the baby can recognize differences of characters only after one year old. As a result of the specific investigation by the applicant (assignee), it was found that "babies of 6 to 17 months old look interestingly at the movement of toys emitting sounds and/or being painted colorfully such as a rattle or a flying jenny, and babies of 18 to 24 months old recognize and enjoy the development of a simple story such as peek-a-boo".

Since the indicating design which disappears when the disposable diaper gets wet may guide the baby whose intelligence is grown to a certain extent to a different direction than "departing from the diaper", which should be the right direction (for example, the baby may intentionally wet the diaper so as to enjoy color change of the design). The applicant believes that it is a great outcome for the applicant (assignee) to find a way based on difficult behaviors in a wide range of situations and patterns of behavior of the baby, which are liable to occur during the usage of disposable diapers of the baby.

Furthermore, in order to reduce the physical and mental burden of the diaper changer when he/she changes diapers and to promote a sound development of the baby, it is preferable to find a way to improve the quality of parent-baby communications during the diaper change. According to the study of the applicant, it is more important to make the illustration drastically change and move during the changing time when the diaper changer changes diapers in order to entertain the baby of several months old who needs to use the disposable diaper so as to make the changing time fun than to prepare a huge number of various illustrations based on such background. The inventors have completed the present invention based on the study. The present invention enables the diaper changer to change diapers with ease and to give the baby a good influence for the mental progress.

More specifically, the following is provided according to the present invention.

(1) A disposable diaper comprising at least one predetermined illustration displayed thereon; wherein the disposable diaper is folded into a predetermined shape; wherein the illustration is provided in such a manner that at least a portion of the illustration is hidden with the disposable diaper folded into the predetermined shape; and wherein the hidden portion of the illustration is being exposed as the folded disposable diaper is unfolded.

According to the present invention, since at least one predetermined illustration is displayed on the disposable diaper in such a manner that at least a portion of the illustration is hidden when the disposable diaper is folded into a predetermined shape, the hidden portion of the illustration in the folded state appears as the folded disposable diaper is unfolded.

(2) The disposable diaper according to (1) comprises: a ventral side display face and a dorsal side display face, wherein the illustration is disposed on the ventral side display face or the dorsal side display face; and wherein the illustration is provided so that another predetermined illustration is formed when the disposable diaper is folded into the predetermined form.

According to the present invention, the illustration displayed on the disposable diaper is disposed on the ventral side display face that corresponds to the front area or on the dorsal side display face that corresponds to the back area in a "natural shape" when being worn, so that at least a portion of the illustration is hidden when the disposable diaper is folded in the predetermined shape, and the hidden portion of the illustration is exposed as the folded disposable diaper is unfolded. Therefore, when the disposable diaper with the illustration is unfolded, the illustration displayed on the ventral side display face that corresponds to the front area or the dorsal side display face that corresponds to the back area when in a "natural shape" appears so as to be capable of being recognized clearly. In addition, according to the present invention, since the illustration is provided so that the predetermined illustration is formed even when the disposable diaper is folded into the predetermined shape, the predetermined illustration can be recognized even when the disposable diaper is folded, and thus the baby may have interest in what kind of illustration will appear when changing disposable diapers. Therefore, when the person who changes the disposable diaper (i.e., diaper changer) gives a reply to the baby, mutual communications and eye contact between the baby and the diaper changer increase, and thus the quality of communications may be improved.

The "display face" refers to a face that the user can view when the disposable diaper is in a "natural shape." The "natural shape" includes all shapes in the states that the disposable diaper is folded in a package, that it is unfolded, and that it is in a process of being unfolded from the state of being packed in the package into the state of being unfolded so as to be suitable to be worn. When the disposable diaper is in the "natural shape", the display face, which becomes the surface that is exposed to the user in such "natural shape", is recognized by the user.

(3) The disposable diaper according to (1) or (2) is characterized in that the disposable diaper is folded in a way of folding a top portion of the disposable diaper along a first folding line substantially parallel with a waist opening edge so that an outer part on either ventral side or dorsal side contacts with each other, a way of folding the top portion around the waist opening edge of the disposable diaper inside out along a second folding line substantially parallel with the waist opening edge, a way of folding side portions of the disposable diaper along third and fourth folding lines substantially orthogonal to the waist opening edge so that the side portions of the outer part on either ventral side or dorsal side contact with each other, a way of folding the side portions inwardly along fifth and sixth folding lines substantially orthogonal to the waist opening edge, or a combination thereof.

In the disposable diaper stated in (1) or (2), the state in which the disposable diaper is folded into the predetermined shape means a state of being folded by a way of folding along a folding line parallel with a waist opening edge so that a portion of the outer side of the outer part on either ventral side or dorsal side is brought into contact with each other, a way of folding the portion around the waist opening edge of the disposable diaper inside out along a folding line parallel with the waist opening edge, a way of folding along folding lines substantially orthogonal to the waist opening edge so that side portions of the outer side of the outer part on either ventral side or dorsal side are brought into contact with each other, a way of folding inwardly along folding lines substantially orthogonal to the waist opening edge, and a method of combination thereof. The ventral side stated here means the side that is located on the side of the abdomen of the body when being worn, and the dorsal side means the side that is located on the side of the back of the body when being worn.

(4) The disposable diaper according to any one from (1) to (3) is characterized in that the illustration comprises a first illustration, a second illustration, and a third illustration; wherein the disposable diaper comprises: a first face on which the first illustration is provided, the first face being disposed on one of the ventral side display face and the dorsal side display face; and a second face on which the second illustration is provided, the second face being off from the first face, and wherein the third illustration is formed by folding the disposable diaper into the predetermined form in such a manner that at least a portion of the first illustration on the first face is covered and that the first illustration overlaps with at least a portion of the second illustration on the second face.

According to the present invention, the disposable diaper includes the first face on which the all-in-one first illustration completed independently is disposed on the ventral side display face or the dorsal side display face when the disposable diaper is worn, and the second face, on which the second illustration is disposed, disposed on the different face from the first face , and the all-in-one third illustration which is different from the illustration disposed on the first face. The third illustration is formed by folding the disposable diaper into the predetermined shape so that a portion of or the entire first illustration is covered and overlapping with at least a portion of the second illustration on the second face. Therefore, in a state in which the disposable diaper is folded, the baby recognizes the third illustration, and when the disposable diaper is unfolded, the recognized illustration changes gradually. When the disposable diaper with illustrations is completely unfolded, the first illustration displayed on the first face is recognized. Accordingly, the baby will have interest in such changes in recognized illustrations as the initially-recognized illustration changes as the disposable diaper is unfolded. And finally the different illustration is recognized. In addition, by providing a feature of story to the changing illustrations, the baby will have more interest in these illustrations.

(5) The disposable diaper according to (4) is characterized in that the first face is constituted of the ventral side display face and the second face is constituted of the dorsal side display face, or the first face is constituted of the dorsal side display face and the second face is constituted of the ventral side display face.

According to the present invention, the disposable diaper includes the first face on which the all-in-one first illustration that is completed independently is disposed so that the first face is provided on either one of the ventral side display face and the dorsal side display face when the disposable diaper is worn, and the second face different from the first face on which the second illustration is disposed. The first face and the second face may correspond to the ventral side display face and the dorsal side display face when the disposable diaper is worn. And the all-in-one third illustration different from the illustration disposed on the first face is formed by folding the disposable diaper into the predetermined shape so that a portion of or the entire first illustration on the first face is covered, and the first illustration overlaps with at least a portion of the second illustration on the second face. Therefore, in a state that the disposable diaper is folded before being worn, the third illustration is recognized. Therefore, the baby first recognizes the third illustration, and the recognized illustration changes gradually as the disposable diaper is developed (or unfolded) for wearing. Then, when the disposable diaper is completely unfolded, the baby recognizes the first illustration displayed on the first face. Therefore, the baby will have interest in such changes in the recognized illustrations that the initially-recognized illustration changes gradually as the disposable diaper is unfolded, and that finally another illustration is recognized. In addition, by providing a feature of story to the changing illustrations, the baby will have more interest in these illustrations. Here, the feature of story may refer to a feature that illustrations are arranged to make a story or a scenario.

(6) The disposable diaper according to (5) is characterized in that the disposable diaper is folded in a way of folding the top portion along a folding line parallel to the waist opening edge, in a way of folding the side portions along folding lines substantially orthogonal to the waist opening edge so that a portion of the outer side of the outer part on either ventral side or dorsal side contacts with each other, or in a way of combination thereof.

According to the present invention, the way of folding the disposable diaper according to (5) may be the way of folding along the folding line parallel with the waist opening edge or along the folding lines substantially orthogonal to the waist opening edge so that portions of the outer side of the outer part on either ventral side or dorsal side are brought into contact with each other, or the way of combination thereof.

(7) The disposable diaper according to (4) is characterized in that the second face is provided on an inner face of the disposable diaper, the inner face being disposed on an opposite side from the outer part on the ventral side display face or the dorsal side display face on which the first illustration is provided, and being in contact with a skin of a wearer when the disposable diaper is worn; and wherein the third illustration different from the first illustration is formed by folding the top portion of the disposable diaper inside out along the folding line parallel with the waist opening edge and by overlapping at least a portion of the second illustration with the first illustration.

According to the present invention, the third illustration different from the first illustration is formed by folding a portion around the waist opening edge of the disposable diaper from the inside toward the outside (or inside out) along the folding line parallel with the waist opening edge so that the inside surface of the disposable diaper on which the second illustration is displayed comes outside and overlapping at least a portion of the second illustration with the first illustration. Therefore, when the portion of the disposable diaper folded along the folding line parallel to the waist opening edge is unfolded into a natural state or shape, the recognized illustration changes to the first illustration different from the third illustration displayed in the folded state. Therefore, as described above, the baby will have interest in such changes in the recognized illustration that the initially-recognized illustration changes gradually as the disposable diaper is unfolded and that finally another illustration is recognized. In addition, by providing a feature of story to the changing illustrations, the baby will have more interest in these illustrations.

(8) The disposable diaper according to any one from (1) to (7) is characterized in that the disposable diaper comprises at least two illustrations and the illustrations express a story.

According to the present invention, since the recognized illustration in the folded state changes as the disposable diaper is unfolded when the folded disposable diaper is unfolded for wearing. Then, another illustration is recognized when the disposable diaper is completely unfolded so that the baby will have interest in changes in the recognized illustrations. In addition, when changes in the illustrations express a story, the baby will have more interest to these illustrations.

(9) The disposable diaper according to (4) or (5) is characterized in that the first illustration, the second illustration, and the third illustration express a story, and wherein the third illustration expresses a first part of the story, the first illustration expresses a second part of the story, and the second illustration expresses a third part of the story.

According to the present invention, the first illustration, the second illustration, and the third illustration have a feature of story and the story is constructed in the order of the third illustration displayed in the disposable diaper in the folded state, the first illustration displayed on the display face of the disposable diaper in the unfolded state, and the second illustration displayed on another display face different from the display face on which the first illustration is displayed in the unfolded state. Therefore, when wearing the disposable diaper, the recognized illustrations change from the third illustration to the first illustration while being unfolded from the folded state. And in addition, the illustration to be recognized shifts to the second illustration by exposing another display face (e.g., the opposite side) in the unfolded state, so that a story is recognized. Furthermore, the diaper changer may improve the quality of communications by talking to the baby about the recognizable changes in the illustrations.

(10) The disposable diaper according to any one from (1) to (9) is characterized in that the disposable diaper is designed for a baby younger than 36 months old.

According to the present invention, the disposable diaper is designed for the babies who may discern illustrations and have interest especially in a simple story, and the target user may be the baby younger than 36 months old.

(11) The disposable diaper according to any one from (1) to (10) is characterized in that the disposable diaper is designed for the baby whose weight is less than 15 kg.

According to the present invention, the disposable diaper is designed for the baby who may discern illustrations and have interest especially in a simple story and is younger than 36 months old, and the target user is the baby whose weight is normally less than 15 kg.

(12) The disposable diaper according to any one from (1) to (11) is characterized in that the disposable diaper is pants-shaped.

(13) The disposable diaper according any from (1) to (11) is characterized in that the disposable diaper may be worn by fastening side portions of the disposable diaper with fastening tapes.

BRIEF DESCRIPTION OF THE DRAWINGS

FIG. 3A is a front view of the disposable diaper in the folded state according to an embodiment of the present invention.

FIG. 3B is a front view of the disposable diaper in FIG. 3A.

FIG. 3C is a rear view of the disposable diaper in FIG. 3B.

FIG. 4A is a front view of the disposable diaper in the folded state according to an embodiment of the present invention.

FIG. 4B is a front view of the disposable diaper in FIG. 4A.

FIG. 4C is a rear view of the disposable diaper in FIG. 4A.

FIG. 5A is a front view of the disposable diaper in the folded state according to an embodiment of the present invention.

FIG. 5B is a front view of the disposable diaper in FIG. 5A.

FIG. 5C is a rear view of the disposable diaper in FIG. 5A.

FIG. 28A shows an illustration that can be used according to the present invention.

FIG. 28B shows an illustration that can be used according to the present invention.

FIG. 29A is a perspective view of the disposable diaper in the folded state according to an embodiment of the present invention.

FIG. 29B is a perspective view of the disposable diaper in the folded state according to the embodiment of the present invention.

FIG. 29C is a front view of the disposable diaper according to the embodiment of the present invention.

PREFERRED EMBODIMENTS OF THE INVENTION

Figure 1:
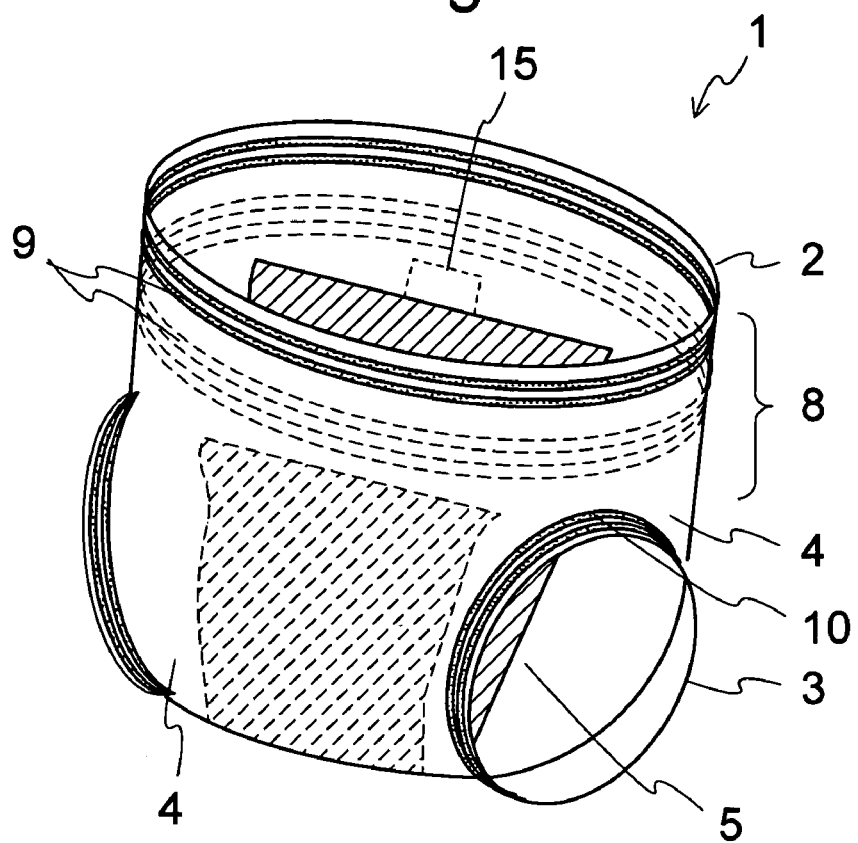
FIG. 1 is a perspective view of the disposable diaper according to an embodiment of the present invention.

FIG. 1 shows a disposable diaper according to an embodiment of the present invention. However, the configuration of the disposable diaper used according to the present invention is not limited to the embodiment.

A disposable diaper 1 shown in FIG. 1 is shaped like a pants. The disposable diaper 1 comprises an outer part 4 forming a waist opening 2 and leg openings 3, and an inner part 5 disposed in the vicinity of the groin portion of the outer part 4 such that the disposable diaper 1 can be formed by bonding the inner part 5 with the outer part 4. A heat seal, an ultrasonic seal, or a hot-melt adhesive agent may be employed for assembling the outer part 4 and the inner part 5.

The inner part 5 comprises an absorbent body and a top sheet disposed on the skin-contacting surface. The top sheet may be made of a water permeable sheet such as a hydrophilic non-woven fabric or a porous plastic. Here, a non-woven fabric refers to a fabric prepared with the spun lace, span bond, needle punch, melt-blown, thermal bond, chemical bond, air-through, etc. As the fibers of the non-woven fabric, polyolefin-, polyester-, or polyamide-based fibers or sheath-core type composite fibers or side-by-side type fibers formed of polyethylene, polypropylene, or polyester may be used.

The absorbent body is composed of hydrophilic fibers and super absorbent polymer. As the hydrophilic fibers, absorbent fibers such as pulp, rayon, acetate, cotton, etc., fibers prepared by making synthetic thermoplastic resin fibers hydrophilic, and so on may be employed. A plastic film may also be provided to prevent leakage of the retained body fluids.

The outer part 4 is composed of one or more sheets so as to realize liquid resistant property, pleasant texture, and air permeability simultaneously. For example, a hydrophobic non-woven fabric, a water-impermeable plastic film, or a sheet formed by laminating such fabric and/or film may be used. The above-mentioned plastic film can be improved in the air permeability and moisture permeability by stretching after mixing a filler.

At a waist portion 8 of the disposable diaper 1, a plurality of elastic members 9, which stretch along the waist opening 2, are provided. A plurality of elastic members 10, which stretch along leg openings 3 are also provided. These elastic members 9 and 10 may be provided between a plurality of sheets that constitute the outer part 4 or may be provided between two sheets in a stretched manner and bonded with the hot melt.

The elastic members 9 and 10 may comprises a plastic sheet composed of natural rubber, synthetic rubber, or synthetic thermoplastic resin.

Figure 2:
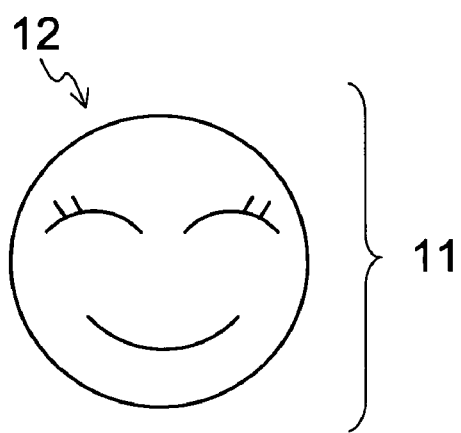
FIG. 2 is a front view of an illustration that may be applied according to the present invention.

An illustration 11 shown in FIG. 2 is disposed on either ventral side display face or dorsal side display face, or both ventral and dorsal side display faces when the disposable diaper 1 is worn so that it can be seen from the outside of the outer part 4.

Now, changes in the illustration from the folded state to the unfolded state and the way of folding the disposable diaper 1 will be described referring to FIGS. 3A to 18B.

FIGS. 3A to 3C show a disposable diaper 1 according to an embodiment of the present invention. The disposable diaper 1 is folded along a folding line parallel to the waist opening edge so that the outer face on the ventral side is brought into contact with each other. The illustration 11 is displayed on the ventral side display face of the disposable diaper 1 as shown in FIG. 3B. In a state that the disposable diaper 1 is folded along a folding line 31, a portion of the illustration 11 is hidden as shown in FIG. 3A, and when the disposable diaper 1 is unfolded for wearing, the entire illustration 11 appears on the ventral side display face as shown in FIG. 3B or in FIG. 4B. The illustration 11 does not appear on the dorsal side display face as shown in FIG. 3C.

FIGS. 4A to 4C show still a disposable diaper 1 according to an embodiment of the present invention. The disposable diaper 1 is folded along folding lines which are substantially orthogonal to the waist opening so that the outer part on the ventral side are brought into contact with each other. The illustration 11 is displayed on the ventral side display face of the disposable diaper 1 as sown in FIG. 4B. In a state that the disposable diaper 1 is folded along folding lines 32, 33, portions of the illustration 11 is hidden as shown in FIG. 4A, and by unfolding the disposable diaper for wearing, the entire illustration 11 appears on the ventral side display face as shown in FIG. 4B. The illustration does not appear on the dorsal side display face as shown in FIG. 4C.

FIGS. 5A to 5C show further a disposable diaper 1 according to an embodiment of the present invention. The illustrations 11 are hidden when the disposable diaper 1 is folded along a folding line 34 as shown in FIG. 5A, and the entire illustrations 11 appear on the ventral side display face as shown in FIG. 5B by unfolding the disposable diaper for wearing. Neither illustration appears on the dorsal side display face as shown in FIG. 5C.

Figure 6A:
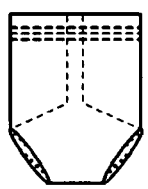
FIG. 6A is a front view of the disposable diaper in the folded state according to an embodiment of the present invention.
Figure 6B:
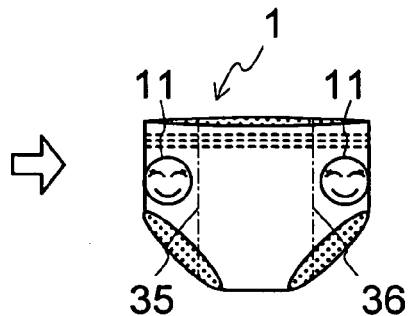
FIG. 6B is a front view of the disposable diaper in FIG. 6A.
Figure 6C:
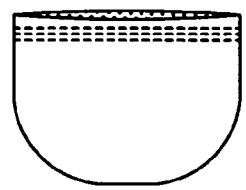
FIG. 6C is a rear view of the disposable diaper in FIG. 6C.

FIGS. 6A to 6C show still a disposable diaper 1 according to an embodiment of the present invention. The disposable diaper 1 is folded inwardly along folding lines which are substantially orthogonal to the waist opening edge. The illustrations 11 are hidden in a state that the disposable diaper 1 is folded along the folding lines 35 and 36 as shown in FIG. 6A, and the entire illustrations 11 appear on the ventral side display face by unfolding the disposable diaper for wearing as shown in FIG. 6B. Neither illustration appears on the dorsal side display face as shown in FIG. 6C.

Figure 7A:
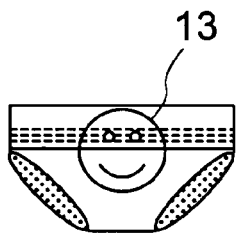
FIG. 7A is a front view of the disposable diaper in the folded state according to an embodiment of the present invention.
Figure 7B:
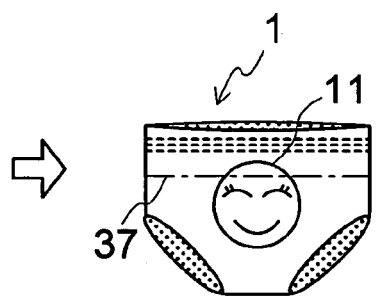
FIG. 7B is a front view of the disposable diaper in FIG. 7A.
Figure 7C:
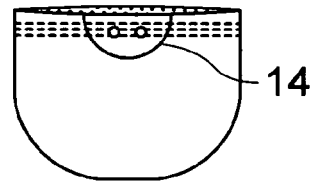
FIG. 7C is a rear view of the disposable diaper in FIG. 7A.

FIGS. 7A to 7C show disposable diaper 1 according to an embodiment of the present invention. The disposable diaper 1 comprises a first illustration 11 displayed on a first face that corresponds to the ventral side display face as shown in FIG. 7B, and a second illustration 14 is displayed on a second face that corresponds to the dorsal side display face as shown in FIG. 7C. In a state that the disposable diaper 1 is folded along a folding line 37, a different illustration 13 from either illustration 11 or 14 is formed as a third illustration 13, which is combined with the illustrations 11 and 14, as shown in FIG. 7A. Therefore, when the disposable diaper 1 is unfolded for wearing, the entire illustration 11 appears on the ventral side display face as shown in FIG. 7B.

Figure 8A:
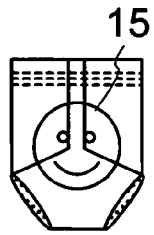
FIG. 8A is a front view of the disposable diaper in the folded state according to an embodiment of the present invention.
Figure 8B:
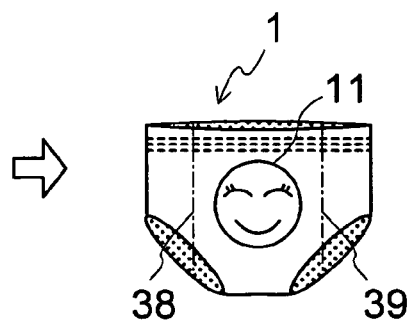
FIG. 8B is a front view of the disposable diaper in FIG. 8A.
Figure 8C:
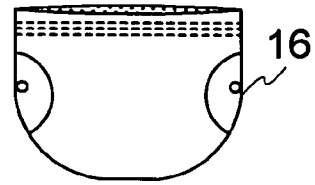
FIG. 8C is a rear view of the disposable diaper in FIG. 8A.

FIGS. 8A to 8C show a disposable diaper 1 according to an embodiment of the present invention. The illustration 11 is shown on the ventral side display face of the disposable diaper 1 as shown in FIG. 8B, and illustrations 16 are displayed at a vicinity of either side portion on the dorsal side display face as shown in FIG. 8C. As shown in FIG. 8A, in a state that the disposable diaper 1 is folded along folding lines 38 and 39, a substantially complete another illustration 15 (third illustration) emerges as a combined illustration with the illustrations 11, 16. Therefore, when the disposable diaper 1 is unfolded or unfolded for wearing, the entire illustration 11 appears on the ventral side display face as shown in FIG. 8B.

Figure 9A:
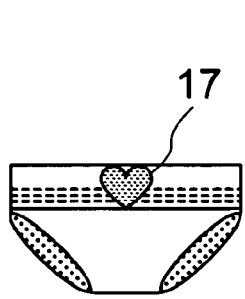
FIG. 9A is a front view of the disposable diaper in the folded state according to an embodiment of the present invention.
Figure 9B:
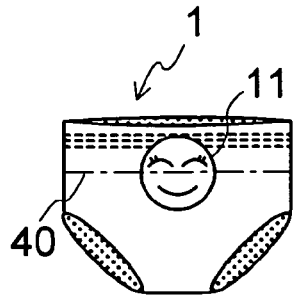
FIG. 9B is a front view of the disposable diaper in FIG. 9A.
Figure 9C:
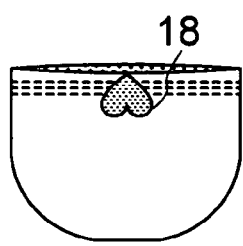
FIG. 9C is a rear view of the disposable diaper in FIG. 9A.

FIGS. 9A to 9C show a disposable diaper 1 according to an embodiment of the present invention. As shown in FIG. 9B, the illustration 11 (first illustration) is displayed on the ventral side display face of the disposable diaper 1, and another illustration 18 (second illustration) is displayed near the waist opening on the dorsal side display face as shown in FIG. 9C. In a state that the disposable diaper 1 is folded along a folding line 40, the illustration 17, which is the upside-down second illustration 18 and is completely different from the illustration 11, appears as shown in FIG. 9A. Therefore, when the disposable diaper 1 is unfolded for wearing, the entire illustration 11 appears on the ventral side display face as shown in FIG. 9B. In this case, the illustration 17 substantially completed in the folded state could be a stand-alone illustration or a combined illustration which is completed by being combined with part of the illustration 11.

Figure 10A:
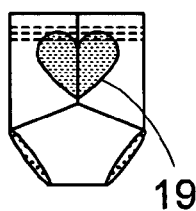
FIG. 10A is a front view of the disposable diaper in the folded state according to an embodiment of the present invention.
Figure 10B:
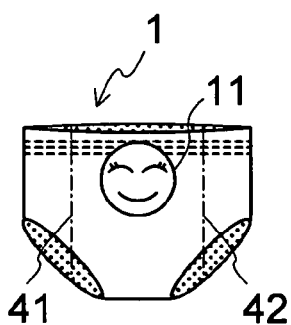
FIG. 10B is a front view of the disposable diaper in FIG. 10A.
Figure 10C:
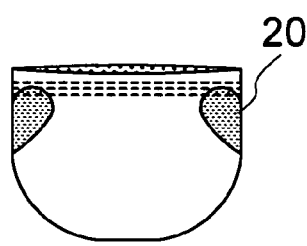
FIG. 10C is a rear view of the disposable diaper in FIG. 10A.

FIGS. 10A to 10C show still a disposable diaper 1 according to an embodiment of the present invention. The illustration 11 (first illustration) is displayed on the ventral side display face of the disposable diaper 1 as shown in FIG. 10B, and illustrations 20 (second illustrations) are displayed near side portions on the dorsal side display face as shown in FIG. 10C. As shown in FIG. 10A, in a state that the disposable diaper 1 is folded along folding lines 41 and 42, another illustration 19 (third illustration) which has nothing to do with the illustration 11 appears. There fore, when the disposable diaper is unfolded for wearing, the entire illustration 11 appears on the ventral side display face as shown in FIG. 10B. In this case, the illustration 19 which is substantially completed in the folded state may be an illustration which is completed by being combined with a part of the illustration 11 or which does not share any parts with the illustration 11 at all.

Although the illustration 11 (first illustration) is displayed on the ventral side display face, and the disposable diaper is folded frontward in these embodiment described above, the illustration 11 (first illustration) may be displayed on the dorsal side display face and the disposable diaper may be folded backward.

As shown in FIGS. 11A to 18B, part of or the entire illustration 11 may be disposed on the outer face of the outer enclosure or the inner face of the outer enclosure so that the illustration 11 can be viewed from the outside when the disposable diaper 1 is folded in the predetermined way. The predetermined folding way may be the way shown from FIGS. 7A to 7C.

Figure 11A:
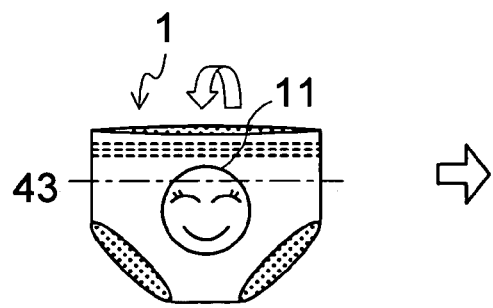
FIG. 11A is a front view of the disposable diaper according to an embodiment of the present invention.
Figure 11B:
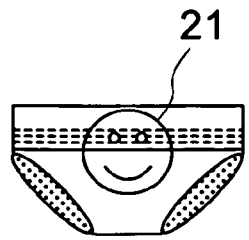
FIG. 11B is a front view of the disposable diaper in FIG. 11A folded along a folding line.

For example, there is a way of folding the disposable diaper along a folding line 43 parallel with the waist opening 2 edge so that the outer portions of either the outer part on the ventral side or on the dorsal side are brought into contact with each other as shown in FIGS. 11A and 11B. In this case, the illustration displayed on the dorsal side display face overlaps the illustration 11 displayed on the ventral side display face of the disposable diaper to complete another combined illustration 21.

Figure 12A:
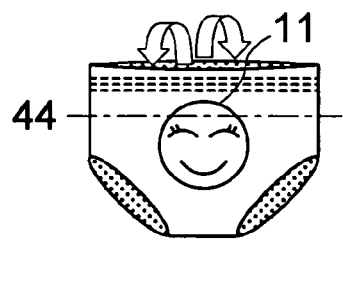
FIG. 12A is a front view of the disposable diaper according to an embodiment of the present invention.
Figure 12B:
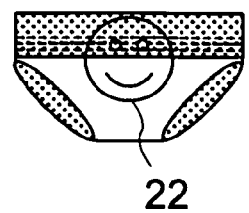
FIG. 12B is a front view of the disposable diaper in FIG. 12A folded along a folding line.

There is also a way of folding the waist opening of the disposable diaper partly from the inside toward the outside along a folding line 44 parallel with the waist opening 2 as shown in FIGS. 12A and 12B. In this case, the second illustration displayed on the inside of the disposable diaper 1 overlaps the first illustration 11 displayed on the ventral side display face to complete a third illustration 22. Expression of smiling eyes of the first illustration 11 differs from that of the third illustration 22.

Figure 13A:
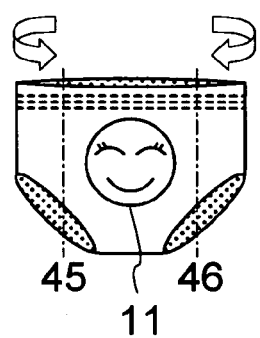
FIG. 13A is a front view of the disposable diaper according to an embodiment of the present invention.
Figure 13B:
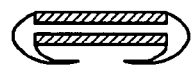
FIG. 13B is a plan view of the disposable diaper in FIG. 13A folded along a folding line.
Figure 13C:
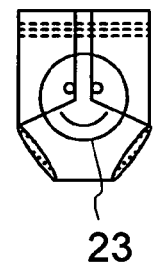
FIG. 13C is a front view of the disposable diaper in FIG. 13A folded along folding lines.

There is also a way of folding the disposable diaper 1 along folding lines 45 and 46 which are substantially orthogonal to the waist opening 2 edge so that the outer portions of the outer part on either ventral side or dorsal side are brought into contact with each other as shown in FIGS. 13A to 13C. In the case of FIGS. 13A to 13C, the second illustration displayed on the dorsal side display face of the disposable diaper 1 overlaps the first illustration 11 displayed on the ventral side display face to complete a third illustration 23. Expression of the smiling eyes of the first illustration 11 differs from that of the third illustration 23.

Figure 14A:
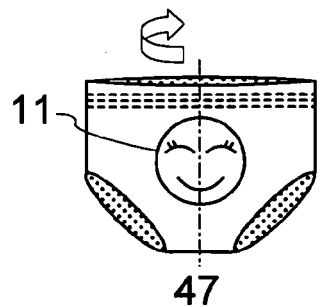
FIG. 14A is a front view of the disposable diaper according to an embodiment of the present invention.
Figure 14B:
FIG. 14B is a front view of the disposable diaper in FIG. 14A folded along a folding line.

As shown in FIGS. 14A and 14B, when the disposable diaper is folded along a folding line 47 which is substantially orthogonal to the waist opening 2 edge, the illustration 11 displayed on the ventral side is hidden since the illustration is not shown on the dorsal side.

Figure 15A:
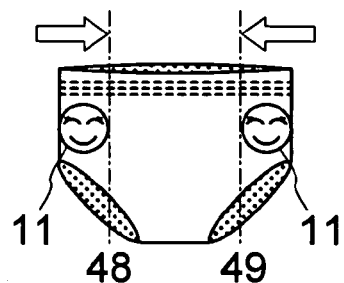
FIG. 15A is a front view of the disposable diaper according to an embodiment of the present invention.
Figure 15B:
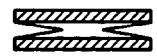
FIG. 15B is a plan view of the disposable diaper in FIG. 15A folded along folding lines.
Figure 15C:
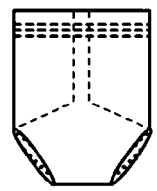
FIG. 15C is a front view of the disposable diaper in FIG. 15A folded along the folding lines.

As shown in FIGS. 15A to 15C, there is a way of folding the disposable diaper inwardly along folding lines 48 and 49 which are substantially orthogonal to the waist opening 2 edge. In this case, the illustrations 11 displayed on the ventral side are bent inwardly such that the illustrations 11 are facing the other faces on dorsal side bent inwardly, respectively. Therefore, the illustrations 11 are hidden therein when the disposable diaper 1 is folded inwardly along the folding lines 48 and 49.

In this manner, when the folding way and the positions of the illustrations to be displayed on the ventral side and/or the dorsal side are suitably combined, the folded disposable diaper has the illustrations to be recognized changing by unfolding the disposable diaper, which provides a feature of story. Conversely, the illustrations to be recognized change by folding the unfolded disposable diaper, which provides a feature of story. In other words, when the diaper changer who changes the diaper shows a baby the disposable diaper having the illustration 11 drawn on the ventral side or on the dorsal side and the substantially completed illustration, which provide a feature of story, the illustrations having the feature of story can more preferably attract the baby so as to distract the baby from changing diapers.

The illustration may be provided by directly printing it on a non-woven fabric or a film on the outermost side when viewed from a viewer of the illustration, or by attaching to the diaper a film on which the illustration is printed beforehand. These illustrations are preferably provided in a size of an outer frame of 4 cm square, and are more preferably drawn with at least one color which has an absolute value of at least 20 of either 'a' or 'b' of L*a*b* color system defined in JIS Z8726. Since the eyesight of the baby younger than thirty six (36) months old is in the order of 0.04-0.08 for the babies of six months old, 0.2-0.25 for the babies of 12 months old, and 0.5-0.6 for the babies of 24 months old, it is said that the illustration which is smaller than the size specified above or the illustration which is drawn only in colors which are lower in color hue than that specified above can hardly be recognized by the baby whose eyesight is not matured.

In order to prevent the printed illustration from fading by being physically rubbed, it is also possible to adhere a non-woven fabric over the printed illustration. In this case, the specific weight of the non-woven fabric is preferably between 5 g/m$^2$ and 25 g/m$^2$ so that the illustration can sufficiently be seen through the non-woven fabric. An adhesive tape is provided on a portion of the outer face of the outer part for holding the rolled-up used disposable diaper by sticking on the diaper so as to make it easier to throw the diaper away. The adhesive tape is preferably provided on the surface substantially on the dorsal side in order to keep the baby from playing the tape during fastening the diaper with the tape, and it may be preferable to provide two or more adhesive tapes so as to ensure fastening the used disposable diaper with the tapes.

The adhesive tape is formed by applying adhesive agent on a plastic film, and is provided with a portion without applied adhesive agent for providing a gripping portion at one end. The adhesive tape is provided on the disposable diaper such that the adhesive agent on the tape contacts the separating film which is directly fixed on the outer face of the enclosure of the disposable diaper. In order to ensure a required length, the tape may be fixed in a Z-folded manner, or may be made of a stretchable tape material. The tape is preferably arranged so as not to overlap the illustration on the outer face of the enclosure. It is preferable that at least a portion of the tape which overlaps with the illustration is transparent so that the illustration is readily visible.

The communications between the baby and the diaper changer who changes the disposable diaper during the changing time were evaluated.

The diaper change experiments were conducted using the disposable diapers shown in FIGS. 16 to 18B.

Figure 16:
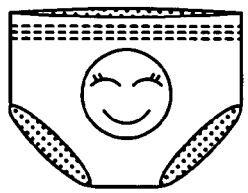
FIG. 16 is a front view of the disposable diaper in the folded state according to an embodiment of the present invention.
Figure 17A:
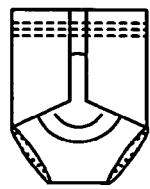
FIG. 17A is a front view of the disposable diaper in the folded state according to an embodiment of the present invention.
Figure 17B:
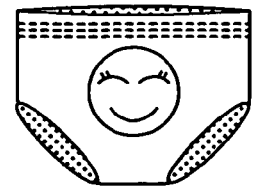
FIG. 17B is a front view of the disposable diaper in FIG. 17A in an unfolded state.
Figure 18A:
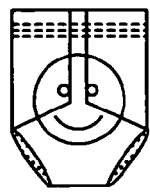
FIG. 18A is a front view of the disposable diaper in the folded state according to an embodiment of the present invention.
Figure 18B:
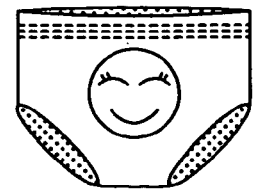
FIG. 18B is a front view of the disposable diaper in FIG. 18B in an unfolded state.

FIG. 16 is a comparative example, FIGS. 17A and 17B show Example 1, and FIGS. 18A and 18B show Example 2. In the Example 1, there is provided a pants type disposable diaper having an illustration on the ventral side and being folded along folding lines which are orthogonal to a waist opening edge so as to hide the illustration. In the Example 2, there is provided a disposable diaper having other illustrations overlapping with the illustration of Example 1 partially when the diaper is folded along folding lines. In the comparative example, there is provided a pants type disposable diaper having an illustration disposed on the ventral side.

The main illustration is provided at the substantially center portion to a size filling an 8 cm by 8 cm square frame.

The time period for changing the disposable diaper refers to a period of time required for the processes comprising preparing a new diaper, bringing a baby closer, removing an old diaper the baby is wearing, cleaning the skin between his/her legs, putting a new diaper, and throwing the used disposable diaper.

(Mutual action between the baby and the diaper changer) end of diaper change=Σ(mutual action signal value)×(duration (second)) start of diaper change In order to quantify and verify communication within the changing time of the disposable diaper, an index of "Mutual action between the baby and the diaper changer" is utilized.

The signal value refers to all approach for transmitting his/her intension or emotion, such as crying, smiling, or raising his/her voice, which are transmitted from the baby or the diaper changer.

Here, the signal value is set one (1) if anything is transmitted from the baby. The signal value is set positive if a positive emotion such as joy or feeling of pleasure is transmitted by the baby. The signal value is set negative if a negative emotion such as feeling of unpleasant or pain is transmitted by the baby. The positive emotion such as joy and feeling of pleasure is judged by the actions such as smiling, raising a cheerful voice, gripping something, playing by putting the gripped subject in his/her mouth, and approaching toward the diaper changer spontaneously. The negative emotion such as feeling of unpleasant or pain is judged from the actions such as crying, running away, getting frustrated, and getting angry. When it is recognized that the diaper changer responds to the signal transmitted by the baby, the absolute value is doubled (to become two (2)).

For example, assuming that the period in which the diaper changer holds down the baby who is crying and running away while the diaper changer is trying to bring the baby closer is thirty (30) seconds, the period in which the baby smiles and the diaper changer talks to the baby during a period of time for changing into a new disposable diaper is twenty (20) seconds, and the period in which the baby raises a cheerful goo-goo voice while the diaper changer is away from the baby for throwing the used disposable diaper is 10 seconds; the value of mutual action between the baby and the diaper changer may be given by:

(Mutual action between the baby and the diaper changer)=(−2)×30+(+2)×20+(+1)×10 =−10

The higher value of mutual action between the baby and the diaper changer in the positive direction may refer to the longer period in which the communications between the baby and the diaper changer are continued.

The results of evaluation are summarized in Table 1. The evaluation was made with two pairs in each class categorized by the baby's age such as 6 to 12 months old, 12 to 18 months old, 18 to 24 months old, and 24 to 36 months old.

TABLE 1

| | Mutual action between baby and diaper changer | | |
|---|---|---|---|
| Lunar Age | Comparative Example | Example 1 | Example 2 |
| -12 months | 10 | 80 | 110 |
| 12-18 month | 10 | 320 | 350 |
| 18-24 months | 20 | 105 | 200 |
| 24-36 months | 15 | 40 | 80 |

The mutual action value between the baby and the diaper changer is significantly higher in the case of Example 1 than the comparative example, and the value of Example 2 is higher than that of Example 1. That is, the data show that communications of higher quality were achieved during changing the disposable diaper in case of the Examples in comparison with the comparative example.

For example, relativity between a plurality of illustrations that appear on the disposable diaper in the folded state and that appear on the disposable diaper in the unfolded state may be as follows:

an action that a character makes changes;

an item in a character's hand changes;

the background around the character changes;

a distance to the character from a specific point of view changes;

facial expressions of a character changes the state of the character changes an irreversible transient of time is expressed under the aforementioned assumption The relativity between the aforementioned plurality of illustrations will be shown in FIGS. 19A to 28B.

Figure 19A:
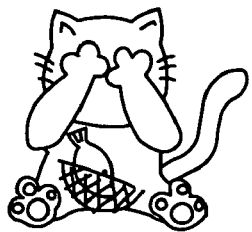
FIG. 19A shows an illustration that can be used according to the present invention.
Figure 19A:
Figure 19B:
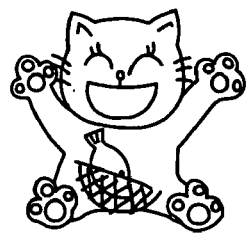
FIG. 19B shows a illustration that can be used according to the present invention.

Illustrations shown in FIGS. 19A and 19B represent that a character plays "peek-a-boo." In other words, these illustrations have such feature of story that the action of the character changes.

Figure 20A:
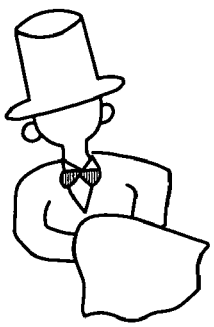
FIG. 20A shows an illustration that can be used according to the present invention.
Figure 20A:
Figure 20B:
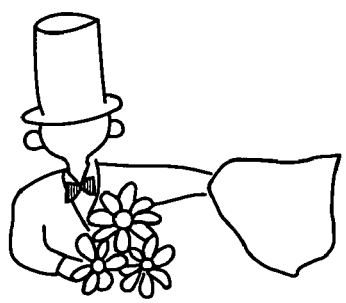
FIG. 20B shows an illustration that can be used according to the present invention.

Illustrations shown in FIGS. 20A and 20B represent that flowers appear in the character's hand when a handkerchief is removed from his hand. In other words, these illustrations have such feature of story that the item in the character's hand changes.

Figure 21A:
FIG. 21A shows an illustration that can be used according to the present invention.
Figure 21A:
Figure 21B:
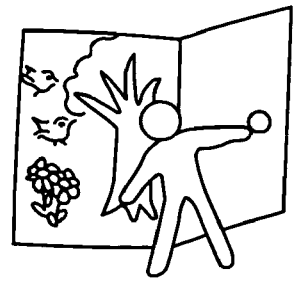
FIG. 21B shows an illustration that can be used according to the present invention.

Illustrations shown in FIGS. 21A and 21B represent that nature appears right in front when the character opens the door of the house. In other words, these illustrations have such feature of story that the background around the character changes.

Figure 22A:
FIG. 22A shows an illustration that can be used according to the present invention.
Figure 22B:
FIG. 22B shows an illustration that can be used according to the present invention.
Figure 22B:
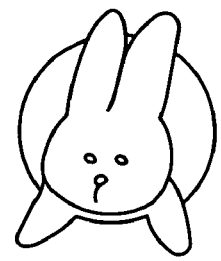

Illustrations shown in FIGS. 22A and 22B represent that a rabbit running in the distance came to right in front. In other words, these illustrations have such feature of story that the distance to the character from a specific point of view changes.

Figure 23A:
FIG. 23A shows an illustration that can be used according to the present invention.
Figure 23B:
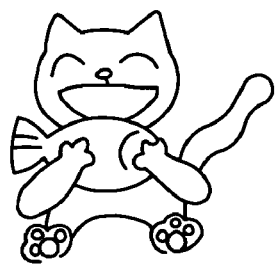
FIG. 23B shows an illustration that can be used according to the present invention.
Figure 23B:
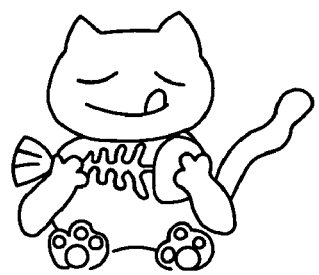

Illustrations shown in FIGS. 23A and 23B represent a delighted face expression of a character before eating fish and a satisfied face expression after eating fish. In other words, these illustrations have such feature of story that facial expression of the character changes. At the same time, this illustration also has such feature of story that an item in the character's hand changes. Furthermore, this illustration also has such feature of story that an irreversible transient of time is expressed.

Figure 24A:
FIG. 24A shows an illustration that can be used according to the present invention.
Figure 24B:
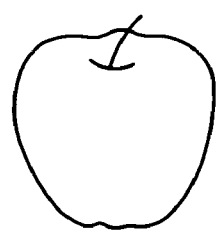
FIG. 24B shows an illustration that can be used according to the present invention.
Figure 24B:

Illustrations shown in FIGS. 24A and 24B represent that an apple changes to an apple core. In other words, these illustrations have such feature of story that the state changes. At the same time, this illustration also has such feature of story that an irreversible transient of time is expressed.

Figure 25A:
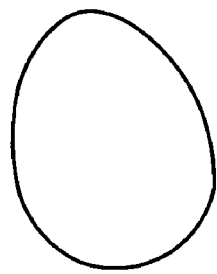
FIG. 25A shows an illustration that can be used according to the present invention.
Figure 25A:
Figure 25B:
FIG. 25B shows an illustration that can be used according to the present invention.

Illustrations shown in FIGS. 25A and 25B represent hatching of a baby bird. In other words, these illustrations have such feature of story that a process of growth is expressed. At the same time, this illustration has a feature of story that expresses an irreversible transient of time.

Figure 26A:
FIG. 26A shows an illustration that can be used according to the present invention.
Figure 26A:
Figure 26B:
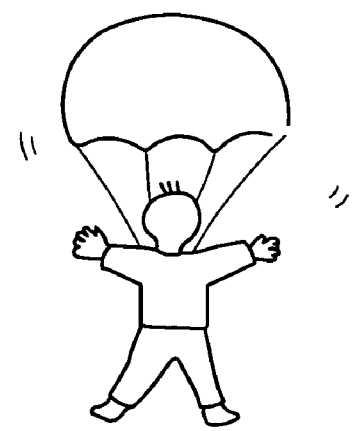
FIG. 26B shows an illustration that can be used according to the present invention.

Illustrations shown in FIGS. 26A and 26B represent that a character flying in the sky opens a parachute. In other words, these illustrations have such feature of story that an action of the character changes. At the same time, this illustration has a feature of story that expresses an irreversible transient of time.

Figure 27A:
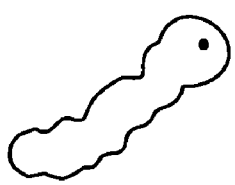
FIG. 27A shows an illustration that can be used according to the present invention.
Figure 27A:
Figure 27B:
FIG. 27B shows an illustration that can be used according to the present invention.

Illustrations shown in FIGS. 27A and 27B represent that a caterpillar changes into a butterfly. In other words, these illustrations have a feature of story that describes a process of growth. At the same time, this illustration has such feature of story that an irreversible transient of time is expressed.

Illustrations shown in FIGS. 28A and 28B represent that a bud opens and blooms. In other words, these illustrations have such feature of story that a process of growth is expressed. At the same time, this illustration has a feature of story that expresses an irreversible transient of time.

In the disposable diapers provided with the illustrations shown in FIGS. 19A to 28B displayed thereon, the hidden illustrations appear by being changed from the folded state to the unfolded state. Thus, a story can be developed in two frames by changing the disposable diaper from the folded state to the unfolded state.

Now, a disposable diaper according to the second embodiment of the present invention will be described.

Figure 30A:
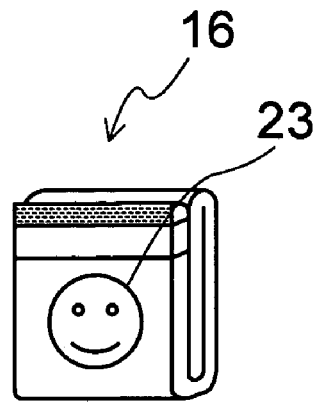
FIG. 30A is a perspective view of the disposable diaper in the folded state according to an embodiment of the present invention.
Figure 30B:
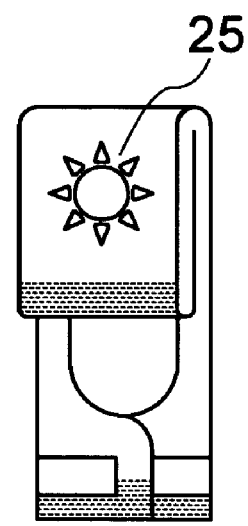
FIG. 30B is a perspective view of the disposable diaper in the folded state according to the embodiment of the present invention.

FIGS. 29A to 29C show the second embodiment of the disposable diaper according to the present invention, and FIGS. 30A and 30B show a disposable diaper according to another embodiment.

Shown in FIG. 29C is a disposable diaper 16 having a form that can be worn by fastening the sides by fastening tapes 22, having an illustration on the outer part of the disposable diaper. The disposable diaper 16, though the configuration of the disposable diaper is not specifically limited to this, has a form including waist members 17, 17' constituting a waist member when being worn at the top and the bottom, and a mid section 18 having recessed portions for forming leg openings when being worn, and a portion corresponding to the inner part of the disposable diaper shown in FIG. 1 includes a top sheet that corresponds to the skin-contacting surface (body side face) when being worn and an absorbent body.

As the top sheet, as described in the above embodiment, a water permeable sheet such as hydrophilic non-woven fabric or porous plastic is used. The non-woven fabric stated here includes those formed by a manufacturing process such as spun bond, spun lace, needle punch, melt blown, thermal bond, chemical bond, and air-through. Fibers of the non-woven fabric may be polyolefin type, polyester type, or polyamide type fiber, sheath-core composite fiber or side-by-side fiber composed of polyethylene, polypropylene, or polyester.

The absorbent body is composed of hydrophilic fiber and super absorbent polymer, as described above, disposed on the back side (opposite side to the body side) of the top sheet. The hydrophilic fiber employed includes absorbent fibers such as pulp, rayon, acetate, or cotton, and fibers obtained by making thermoplastic synthetic resin fiber hydrophilic. A plastic film may be provided for preventing retained body fluid from leaking.

The outer part 19 on the opposite side to the body side is formed of a back sheet including one or more sheets for realizing liquid resistant property, softness and tenderness for the skin, and air permeability simultaneously. For example, a hydrophobic non-woven fabric, an impermeable plastic film, or a lamination thereof may be used. The plastic film can be enhanced in air permeability and moisture permeability by mixing filler and then drawing.

Extremities of the respective waist members 17, 17' are provided with a plurality of elastic members 20 that extend in the lateral direction and both outer side edges of the mid section 18 are provided with a plurality of elastic members 21 that extend along the recessed portions. These elastic members 20, 21 are provided between the plurality of sheets that constitutes the outer part 19, and are joined between two sheets by hot melt in a state of being expanded.

The waist member 17 that corresponds to the back body (dorsal side display face) when being worn is provided with fastening tapes 22 at the ends in the longitudinal direction so as to extend outwards. The waist member 17' that corresponds to the front body (ventral side display face) when being worn is provided with a fastening tape 22' in the longitudinal direction. These tapes also serve as post-processing tape to be used after use.

As shown in FIG. 29C, the outer part 19 is provided with illustrations 23, 24 at the waist members 17, 17'. Such tape-type disposable diaper is normally packed in the folded state, and a illustration shown in FIG. 29A is displayed in a state of being folded. The folded disposable diaper is unfolded when wearing. When being unfolded, the illustration changes in sequence as shown by arrows in FIGS. 19A to 27B. In other words, when the disposable diaper is unfolded downward from the folded state, a face illustration 24 in the upside-down state appears as shown in FIG. 29B. Then, when the disposable diaper is completely unfolded, the face illustrations 23 and 24 appear on the outer part 19 of the disposable diaper 16 in the upside-down relation with each other as shown in FIG. 29C. In this manner, the illustration to be recognized on the folded disposable diaper changes as it is unfolded.

Figure 31A:
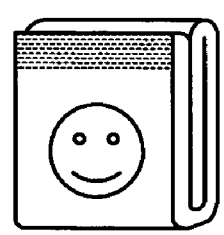
FIG. 31A is a perspective view of the disposable diaper in the folded state according to an embodiment of the present invention.
Figure 31B:
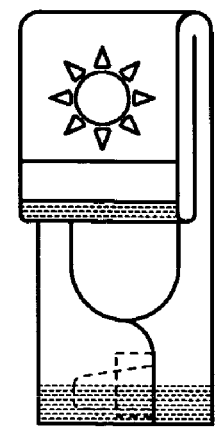
FIG. 31B is a perspective view of the disposable diaper in the folded state according to the embodiment of the present invention.
Figure 32A:
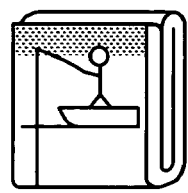
FIG. 32A is a perspective view of the disposable diaper in the folded state according to an embodiment of the present invention.
Figure 32A:
Figure 32B:
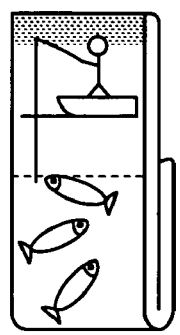
FIG. 32B is a perspective view of the disposable diaper in the folded state according to the embodiment of the present invention.
Figure 32B:
Figure 32C:
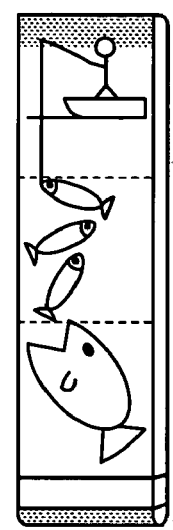
FIG. 32C is a perspective view of the disposable diaper in the folded state according to the embodiment of the present invention.
Figure 33A:
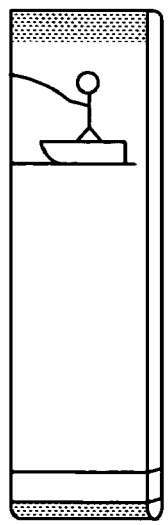
FIG. 33A is a front view of the disposable diaper in the folded state according to an embodiment of the present invention.
Figure 33A:
Figure 33B:
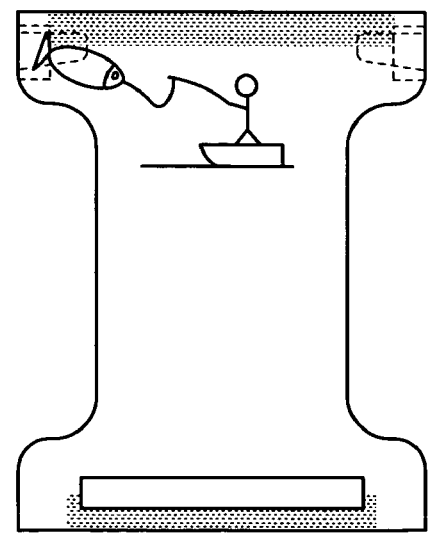
FIG. 33B is a front view of the disposable diaper according to the embodiment of the present invention.

FIGS. 30A and 30B are the same as FIGS. 29A and 29B, however, the illustration shown thereon is different. The tape-type disposable diaper 16 in FIG. 30A includes a illustration 25 without distinction of orientation displayed on the waist member (backside) of the outer part as shown in FIGS. 30A and 30B. Such illustration may be displayed on the waist member of the outer part as shown in FIGS. 31A and 31B, or maybe displayed on any part of the waist member. The construction, material, and so on of the disposable diaper 16 are the same as those of the disposable diaper shown in FIGS. 18A and 18B. Then, as shown in FIGS. 32A to 32C, and FIGS. 33A to 33C, it is also possible to express a story by illustrations which appear in sequence as the folded disposable diaper is unfolded.

In this manner, when the next development is recognized by unfolding the folded disposable diaper step by step, the baby is entertained. Then, when the diaper changer replies to the baby, mutual communications and eye contact are established.

The layout of these illustrations is not limited as long as they are arranged so as to be recognized from the outside of the disposable diaper as described in conjunction with the embodiments described above. For example, it may be printed directly on the non-woven fabric or film that constitutes the outer part 19, or it is also possible to adhere a film on which an illustration is printed beforehand on the film that constitutes the outer part 19. And, it may be arranged on the inner side in the manner described above.

Preferably, the fastening tapes 22 and 22' are arranged so as not to overlap the character on the outer face of the outer part 19, or at least the portion of the fastening tapes 22 and 22' which may overlap with the illustration is transparent so that the illustration is readily visible.

As described above, according to the present invention, when the diaper changer shows the folded disposable diaper to the baby, and then, unfolds the disposable diaper and shows the appeared illustrations to the baby, the baby is entertained. When the diaper changer replies to the baby, mutual communications and eye contact increase spontaneously, and thus the quality of communications is improved. Therefore, the diaper changer may have deeper feeling of commitment with respect to the baby, and a healthy growth of the baby is promoted.

In addition, since the diaper can be changed in a state with the baby in a good temper, physical and mental burden by changing of diapers may be alleviated.

What is claimed is:

1. A disposable diaper, wherein the disposable diaper is a pants type disposable diaper having a waist opening, two leg openings and opposite ventral and dorsal sides, said diaper comprising at least one predetermined illustration displayed on an outer surface thereof;
   wherein the disposable diaper has a folded state in which at least a portion of the illustration is hidden;
   wherein the diaper further has a unfolded state in which the hidden portion of the illustration is exposed;
   wherein the disposable diaper in the folded state has opposite side portions of the disposable diaper being folded along first and second folding lines substantially orthogonal to an edge of the waist opening, wherein the outer surface of said diaper on either said ventral side or said dorsal side contacts with itself; and
   wherein the illustration comprises a first illustration, a second illustration, and a third illustration;
   wherein the disposable diaper comprises:
   a first face on which the first illustration is provided, the first face being the outer surface of said diaper on one of the ventral side and the dorsal side of the diaper; and
   a second face on which the second illustration is provided, the second face being other than the first face; and
   wherein the third illustration is visible when the diaper is in the folded state in which the hidden portion of the first illustration on the first face is covered with at least a portion of the second illustration on the second face.

2. The disposable diaper according to claim 1, wherein the second face is the outer surface of said diaper on the other one of the dorsal side and the ventral side.

3. The disposable diaper according to claim 1, wherein the first illustration and the third illustration express a story, and
   wherein the third illustration expresses a first part of the story, and the first illustration when fully visible expresses a second part of the story.

4. The disposable diaper of claim 1,
   wherein, when said diaper is in said folded state, said second illustration partially covers the first illustration and defines together with a uncovered portion of said first illustration the third illustration, and wherein said first illustration when fully visible is different from said third illustration.

5. The disposable diaper according to claim 4, wherein said first illustration when fully visible comprises a character dominantly displayed in said first illustration; and
   in said third illustration, the same character is dominantly displayed, said character being changed in facial expression from one of said first and third illustrations to the other.

6. The disposable diaper according to claim 1, wherein the first illustration is different from the third illustration which is formed when the diaper is in the folded state, the third illustration is changed to the first illustration when said disposable diaper is unfolded from the folded state to the unfolded state.

7. The disposable diaper according to claim 1, wherein said first illustration has a size of about 64 centimeters squared.

8. The disposable diaper according to claim 1, wherein the disposable diaper is configured for a baby younger than 36 months old.

9. The disposable diaper according to claim 1, wherein the disposable diaper is configured for a baby whose weight is less than 15 kg.

10. The disposable diaper according to claim 1, wherein, when the disposable diaper is in the folded state, the edge of the waist opening and a peripheral edge of each of the leg openings are also folded.

11. The disposable diaper according to claim 1, wherein the edge of the waist opening intersects the first and second folding lines; and
    a peripheral edge of each of the leg openings intersects a respective one of said first and second folding line.

12. The disposable diaper according to claim 11, wherein the peripheral edge of each of the leg openings intersects the respective one of said first and second folding line twice.

13. The disposable diaper according to claim 12, wherein
the second illustration is completely located in the side portions of the disposable diaper;
the first illustration is completely located in a central portion of the disposable diaper between said side portion; and
each of the first and second folding lines defines a border between said central portion and a respective one of said side portions.

14. The disposable diaper according to claim 13, wherein the second illustration includes first and second parts each being completely located in one of said side portions of the disposable diaper.

* * * * *